United States Patent [19]

Hamaoka et al.

[11] Patent Number: 4,722,899
[45] Date of Patent: Feb. 2, 1988

[54] PRODUCING HIGHLY SPECIFIC, LOW CROSS-REACTIVE ANTIBODY BY IMMUNIZING WITH COPOLYMER OF D-GLUTAMIC ACID AND LYSINE

[75] Inventors: Toshiyuki Hamaoka, 730-1022, Gakuen-daiwacho 5-chome, Nara-shi, Nara-ken; Kayoko Tateishi, Higashi-Osaka, both of Japan

[73] Assignee: Toshiyuki Hamaoka, Nara, Japan

[21] Appl. No.: 505,892

[22] Filed: Jun. 20, 1983

Related U.S. Application Data

[63] Continuation-in-part of Ser. No. 433,608, Oct. 12, 1982, abandoned, which is a continuation of Ser. No. 253,457, Apr. 13, 1981, abandoned, which is a continuation-in-part of Ser. No. 252,772, Apr. 10, 1981, abandoned.

[30] Foreign Application Priority Data

Apr. 11, 1980 [JP] Japan ................................. 55-48447

[51] Int. Cl.[4] ................... G01N 33/53; G01N 33/531; G01N 33/534
[52] U.S. Cl. .................................... 435/172.2; 435/68; 435/240.27; 436/547; 436/548; 436/804; 436/815; 436/817; 436/818; 436/823; 530/387; 935/89; 935/93; 935/95; 935/102; 935/110
[58] Field of Search ............... 436/547, 548, 804, 815, 436/817, 818, 823; 405/68, 172.2, 240; 935/89, 93, 45, 102, 110; 530/387

[56] References Cited

U.S. PATENT DOCUMENTS

| | | | |
|---|---|---|---|
| 4,156,081 | 5/1979 | Singh | 530/405 X |
| 4,172,124 | 10/1979 | Koprowski | 424/86 X |
| 4,524,025 | 6/1985 | Geltosky | 436/548 X |

OTHER PUBLICATIONS

Kohler, G. et al., Nature 256, 495–497 (1975).
Tateishi, K. et al., Steroids, 36(3), 283–288 (Sep. 1980).

Primary Examiner—Sidney Marantz
Attorney, Agent, or Firm—Wolder, Gross & Yavner

[57] ABSTRACT

A process for producing an antibody having a high specificity to a first antigen and a low cross-reactivity with at least one second antigen, said first antigen comprising a desired antigenic determinant and said second antigen comprising at least one antigenic determinant which is structurally related to said desired antigenic determinant of said first antigen, which process comprises treating a mammal with a copolymer of D-glutamic acid and D-lysine coupled with said second antigen whereby to induce a substantially effective immunological tolerance to said second antigen and then immunizing said mammal with said first antigen. This process results in a higher productivity of a mammal cell capable of producing said desired antibody by culturing said mammal cell, for example, by forming a hybridoma with a suitable tumor cell and implanting the hybridoma into another mammal. The antibody or antiserum of this invention may with advantage be used for immunoassay such as radioimmunoassay.

17 Claims, 1 Drawing Figure

Fig. 1

PRODUCING HIGHLY SPECIFIC, LOW CROSS-REACTIVE ANTIBODY BY IMMUNIZING WITH COPOLYMER OF D-GLUTAMIC ACID AND LYSINE

This application is a continuation-in-part of our earlier copending application Ser. No. 433,608 filed Oct. 12, 1982, now abandoned, which is a continuation of Ser. No. 253,457 filed Apr. 13, 1981 now abandoned, which is a continuation-in-part of Ser. No. 252,772 filed Apr. 10, 1981 now abandoned.

FIELD OF ART

This invention relates to an improved antibody, antiserum containing such antibody and clone for the production of such an antibody and also relates to their production. This invention further relates to a method of immunoassay using such antibody or antiserum.

PRIOR ART

For example, various methods for immunoassay of a number of substances contained in living body of humans and animals are known, which utilize the competitive antigen-antibody reaction by employing a given amount of an antibody and various different amounts of antigens. However, the immunoassay methods of the known types have, in general, the disadvantages that even in cases where the reagent used for immunoassay (antibody) is believed to be highly specific to the substance to be assayed (antigen), the assay specificity tends to be affected by the cross-reactive substances which are structurally related to the substances to be assayed. In order to overcome such difficulty, various improvements have been proposed, which, in general, fall into the following categories: (1) prior to the determination, various cross-reactive substances are eliminated from the assay sample by the use of physico-chemical techniques, and (2) the cross-reactive antibody present in the antiserum is removed before use by an immunoabsorbant. Alternatively, it is possible to use a highly purified antibody having a very high specificity for the substance to be assayed. In order to prepare such an antibody having a highest possible specificity, it has been proposed to bind an antigen, prior to injection into an animal host, onto a carrier at an appropriate site in its chemical structure in such a manner that the relevant determinant site on the antigen to be recognized by the antibody is exposed on the surface of the carrier molecule. The exposure of a specific determinant site thereby stimulates the formation of an antibody having low cross-reactivity. Known methods of this type are, however, still unsatisfactory because of the need for complicated procedures and a synthetizing step. Moreover, in some cases, it is still difficult to avoid the production of cross-reactive antibodies by such methods, and thus such problems may render the immunoassay of the desired substances very difficult.

The present invention is based upon the discovery that it is possible to reduce the amount of the cross-reactive antibody to a minimum and also to obtain an antibody having excellent specificity for a substance, for example, to be assayed by the use of a copolymer of D-glutamic acid and D-lysine (hereinafter referred to as D-GL) coupled with a cross-reactive antigen.

SUMMARY OF THE INVENTION

An object of this invention is to provide an improved antibody having a high specificity and low cross-reactivity, an antiserum containing such an antibody and cells capable of producing such antibodies (hereinafter referred to as clones). This invention is further directed to provide an immunoassay method using such antibody or antiserum.

According to one feature of this invention, there is provided a process for producing an antibody or antiserum having a high specificity to a first antigen comprising a desired antigenic determinant and having a low cross-reactivity with at least one other antigen by immunizing a mammal or by culturing mammal cells capable of producing antibodies, said other antigen comprising at least one antigenic determinant which is structurally related to said desired antigenic determinant of said first antigen, which process comprises treating a mammal with a copolymer of D-glutamic acid and D-lysine coupled with said antigen whereby to induce substantially effective immunological tolerance and subsequently immunizing the mammal with said first antigen.

By the process of the present invention, it is possible to reduce the amount of cross-reactive antibody to a minimum and also to produce the desired antibody or antiserum having improved properties, because D-GL induces a substantially effective immunological tolerance to B cells which serve as the precursor for the production of antibodies. When an animal is treated by the process of this invention, D-amino acid in the living body are not readily metabolized and moreover the activity of T cells to D-GL is hardly induced in the living body. Thus it is believed that when an animal is treated by the process of this invention, such a hapten-D-GL conjugate specifically binds to the surface immunoglobulin receptor on B lymphocytes and renders these cells irreversibly tolerance.

The desired antibody may be obtained in the form of a pure antibody or in the form of an antiserum containing the desired antibody. As the process of the present invention results in the production in the living body of cells of the same genetic constitution which are capable of producing the desired antibodies i.e. clones, it is possible to obtain the desired antibody by culturing the thus-obtained clone in conventional manner. In this respect, it will be appreciated that the clones removed from the living body of the mammal may be used for the production of the desired antibody even in the absence of the initiating mammal because it is well known to combine a suitable clone with a suitable tumour cell to obtain a hybridoma, for example, by combining such a clone with a myeloma cell [for example, Nature, vol. 256, 495–497 (1975); European J. of Immunol., vol. 6, 511–519 (1976); Nature, vol. 266, 550–552 (1977); and Nature, vol. 266, 495 (1977)]. Such a hybridoma is transplanted to or implanted into another mammal and the hybridoma cells propagate continuously to produce a large amount of the desired antibody or the present invention. Thus, it is possible to use such a hybridoma as a new source of the desired antibody.

According to a further feature of the present invention, there is provided an immunoassay method of a substance serving as an antigen, which comprises reacting the said first antigen i.e. the substance to be assayed with an antibody or antiserum of this invention in the presence of said second antigen or antiserum, separating the first antigen from the immune complex thus-obtained, and determining the activity of said first antigen. The immunoassay of the present invention may be effected in conventional manner, for example, by radioimmunoassay or assay by the use of non-isotropic labels such as e.g. enzymes, free radicals, cells, viruses, metal ions, and fluorescent and chemiluminescent groups. The immunoassay method of this invention enable an assay to be effected even in the presence of a cross-reactive antigen.

It is preferred for the purpose of the present invention to use D-GL having a molecular weight of from about 27,000 to about 120,000. The molar ratio of D-glutamic acid to D-lysine is preferably from about 70:30 to about 30:70. Copolymers of this type are commercially available (for example, from Miles-Yeda, U.S.A.), although it is possible to prepare such copolymers in conventional manner, for example, by copolymerizing the N-carboxylic anhydride of γ-alkyl-D-glutamate and the N-caroboxylic anhydride of ε-N-carbobenzyloxy-L-lysine in the presence of a suitable amine, followed by removal of the protecting group.

Various naturally occuring substances may, for example, be used for the production of the antibody for immunoassay. Examples of preferred materials for this purpose include steroids, glucuronates and sulfates thereof; catechol amines; peptides, subunits and related fragments thereof; and various pharmaceutical agents whenever appropriate.

Especially preferred examples of steriods include testosterone (hereinafter referred to as Te), 5α-dihydrotestosterone (hereinafter referred to as DHT), androsterone, etiocholanolone, progesterone, 17α-hydroxyprogesterone, pregnenolone, dehydroepiandrosterone, oestradiol, oestrone, oestriol, aldosterone, deoxycorticosterone, cortisol, cortisone, corticosterone, 11-deoxycortisol, cholic acid, deoxycholic acid, lithocholic acid and conjugated products thereof.

Catecholamines are exemplified by dopamine, norepinephrine, epinephrine and derivatives thereof.

Peptide hormones are exemplified by gastrin, cholecystokinin-pancreozymin, insulin, proinsulin, C-peptide, glucagon, follicle-stimulating hormone (FSH), luteinizing hormone (LH), human chorionic gonadotropin, (HCG), somatostatin, thyroid-stimulating hormone (TSH) and their subunits and related peptides thereof.

Pharmaceutical agents are exemplified by l-propranolol which is a β-blocking agent and l- or d-cyclazocine which is an analgenic agent.

For example, when an anti-Te antibody or antiserum is prepared by conventional immunization methods, DHT acts as the cross-reactive antigen because their structures are closely similar to each other. Similarly, when an anti-DHT antibody or antiserum is prepared, Te acts as the cross-reactive antigen. In this manner, various steroids act as the cross-reactive antigens for other steroids.

The above-mentioned substances are, in general, the haptens or the like i.e. the substances capable of coupling with an antibody but incapable of inducing an immune response or capable of inducing only a weak immune response if they are not coupled with a carrier prior to their administration to a living animal. It is thus necessary to couple them into a suitable carrier in order to induce the formation of antibody. For example, in order to induce an antibody specific for a certain antigen such as anti-testosterone (hereinafter referred to as anti-Te) antibody, this antigen should be coupled with a suitable carrier and used for immunization. However, the anti-Te clones and antibodies thus obtained usually have a strong cross-reactivity with substances having an analogous structure such as DHT. According to this invention, it is possible to inhibit specifically the formation of such cross-reactive anti-DHT clones and antibodies by treating the animal with a substance which is the product of coupling a copolymer of D-GL with a cross-rective antigen, in this case, DHT.

Moreover, it has also been found that an antibody capable of reacting with the specific determinant of the desired antigen is obtained when an animal is treated with a conjugate of D-GL and a peptide analogous to said antigen, or fragment of the peptide being common to that of the desired antigen. An example to demonstrate such as advantage pertaining to this invention include the case of antibodies to an octapeptide which is a C-terminal peptide comprising eight amino acids of cholecystokinin-pancreozymin (hereinafter referred to as CCK) which is a gastro-intestinal hormone. The structure (amino acid sequence) of gastrin (human), CCK and their fragments are shown in Table 1.

TABLE 1

| | |
|---|---|
| Gastrin(human): | (Pyro)Glu—Gly—Pro—Trp—Leu—Glu— |
| | —Glu—Glu—Glu—Glu—Ala—Tyr—Gly— |
| |                                               ($SO_3H$) |
| | —Trp—Met—Asp—Phe—$NH_2$ |
| CCK-33: | Lys—Ala—Pro—Ser—Gly—Arg—Val— |
| | —Ser—Met—Ile—Lys—Asn—Leu—Gln— |
| | —Ser—Leu—Asp—Pro—Ser—His—Arg— |
| | —Ile—Ser—Asp—Arg—Asp—Tyr— |
| |                                            $SO_3H$ |
| | —Met—Gly—Trp—Met—Asp—Phe—$NH_2$ |
| CCK-8-P: | Asp—Tyr—Met—Gly—Try—Met—Asp— |
| |           $SO_3H$ |
| | —Phe—$NH_2$ |
| Pentagastrin: | Gly—Trp—Met—Asp—Phe—$NH_2$ |
| CCK-8-NS: | Asp—Tyr—Met—Gly—Trp—Met—Asp— |
| | —Phe—$NH_2$ |
| Caerulein: | (Pyro)Glu—Gln—Asp—Tyr—Thr—Gly— |
| |                        $SO_3H$ |
| | —Trp—Met—Asp—Phe—$NH_2$ |

Cholecystokinin-pancreozymin (CCK) is a known type of secretory hormones found in the gastrointestinal tract, which stimulates the secretion of the pancreatic enzyme and also causes the contraction of the gallbladder. There is a known polypeptide consisting of 33 amino acids and its biological activity results from the fragement of eight amino acids at the C-terminal of the peptide (CCK octapeptide, hereinafter referred to as CCK-8-P). The sequence of the 5 C-terminal amino acids is the same as the sequence of the 5 C-terminal amino acids of gastrin, a hormone capable of stimulating the secretion of acids in the stomach. It is thus known that the anti-CCK-8-P antibody is highly cross-reactive with gastrin.

It has recently been found, however, that CCK-8-P and its reactive receptor are also present in the brain, and the investigation of the function of this hormone as a neurotransmitter as well as the secretion and its action on various diseases of gastro-intestinal tract is of interest. It is thus important to provide an antibody capable of specifically reacting with CCK-8-P.

Antibody-forming clones and antibodies capable of specifically reacting with CCK-8-P may be obtained according to this invention by administering to an animal a conjugate of D-GL with pentagastrin (i.e. the five amino acids located at the C-terminal end of gastrin and CCK-8-P) so as to inactivate clones which produce antibodies cross-reacting with pentagastrin and gastrin-like compounds and then immunizing said animal with CCK-8-P.

Thus according to this invention, it is also possible to produce gastrin-specific antibody by inhibiting the formation of clones which cross-react with CCK by treating an animal with a conjugate of D-GL and pentagastrin, which is the C-terminal fragment of the desired antigen, and then immunizing said animal with gastrin.

As is apparent from the Examples of this invention appearing hereinafter, it may also be possible to obtain a desired specific antibody by administering to an animal a conjugate of D-GL with a cross-reactive peptide even in the case in which specific antigenic determinant can not easily be removed from the whole peptide by peptide fragmentation.

For instance, Attasi et al demonstrated the composition of the antigenic determinants of lysozyme by using synthesized peptides based on his "surface simulation model" [Attasi M. Z., Immunochemistry, vol. 15, 909–936 (1978)]. In this case, the antigenic determinant is formed of amino acids located at irregular intervals (for example, assuming that the determinant is formed with amino acids A, B, C and D and that there is a peptide having an entirely different amino acid sequence which however, accidentally comprises amino acids B-C which serve to form a stereochemically common antigenic determinant), it is readily possible to amplify selectively a specific clone directed to the antigenic determinant A-D so as to form an antibody directed to the specific site by administering to an animal a substance formed by coupling antigenic determinant comprising amino acids B-C with D-GL and resulting in the elimination of the clones having a cross-reactivity with the antigenic determinant comprising the amino acids B-C.

Such a combined product of D-GL and cross-reactive antigen may be obtained either (1) by coupling the antigen directly with D-GL or (2) by coupling the antigen indirectly with D-GL forming a bridge between antigen and D-GL. For this purpose, various derivatives of the antigen, especially steroid antigens have been made, which derivatives are exemplified by oxime derivatives, succinyl derivatives, and chlorocarboxylic acid derivatives by Erlanger et al [e.g. B. F. Erlanger et al, J. Biol. Chem., 228, 713 (1957)]; carboxylmethylthioether derivatives [A. Weinstein et al., Steroid, 20, 789 (1972)], carboxylmethylether derivatives [P. N. Rao et al, J. Steroid Biochem., 9, 539 (1978)] etc. Preferred coupling methods are exemplified by the carbodiimide method, the mixed anhydride method, the Schotten-Baumann method and the isoxazolium method.

When an $NH_2$ group is introduced into such a compound, the coupling reaction is effected by the glutaraldehyde method, and when an $NH_2$ or SH group is introduced into such a compound, the reaction can be performed by the use of an m-maleimidobenzoyl-N-hydroxysuccinimide ester, succinimidyl-4-(N-maleimidomethylcyclohexane)-1-carboxylate, succinimidyl-4-(p-maleimidophenyl)butyrate and the like or N-succinimidyl-3-(2-pyridyldithio)propionate, N-succinimidyl-(4-azidophenyldithio)propionate and the like. In addition, various other methods conventionally used to couple peptides with other substances in the field of peptide chemistry may also be used for coupling D-GL with an antigen.

The antigens which may be used for the purpose of this invention are in general haptens or the like, and thus it is necessary to couple the antigen before use with a suitable carrier which is used in conventional immunization methods. Preferred carriers for this purpose are exemplified by keyhole limpet haemocyanin (KLH), $\gamma$-globulin and albumin originating from the serum of different animal species used for immunization such as e.g. humans, goats, bovines and the like.

The antigens, their subunits or related fragments should be coupled with a carrier protein in a similar manner to that applied to couple a cross-reactive antigen with D-GL. Thus, the coupling may be accomplished directly or indirectly. In the latter case, the same intermediate as that used for coupling D-GL with the cross-reactive antigen should be used for coupling the desired antigen with a carrier protein.

The immunization treatments may be effected in conventional manner. Depending upon the type of animal used, a saline solution containing an antigen (a combined product of a hapten or the like and carrier) is administered to the animal by intraperitoneal (ip.) injection. Alternatively, it is possible to inject the antigen solution into the foot pad or a subcutaneous site on the back of the animal. At the primary and secondary immunization, the antigen solution is preferably administered in association with complete Freund's adjuvant and incomplete Freund's adjuvant, respectively. After this, the antigen solution is preferably solely administered in the case of smaller animals such as mice and guinea pigs, and complete Freund's adjuvant and incomplete Freund's adjuvant may for example be used in turns together with the antigen solution in the case of larger animals such as the rabbit, goat, horse and the like. The dose may vary, depending upon the combined ratio of the hapten or the like and carrier, and the molecular weight of the carrier and the like. However, it is usually preferred to immunize animals with an antigen at a dose of 1–100 μg/smaller animal e.g. the mouse or 0.1–1 mg/larger animal e.g. the rabbit/once, which may be repeated for example 2–5 times at 2–4 week intervals. Usually 2–3 days before the primary immunization, a conjugate of D-GL and a cross-reactive antigen may be given to the animal, although in some cases, the D-GL conjugate may also given before the secondary and tertiary immunization, depending upon the type of the cross-reactive antigen. The dose of the D-GL conjugate with the cross-reactive antigen may vary, depending upon the combined ratio of the cross-reactive antigen (hapten or the like) to D-GL, sites of coupling, types of intermediate compound and the like, but is preferably in the range of 100–500 μg/smaller animal or 2–10 mg/larger animal. The D-GL conjugate may be dissolved in a saline solution and administered by injection (ip.).

It will be appreciated that the above-mentioned findings have been tested not only in smaller animals but also in larger animals. It is thus important that the same results have been found in both smaller and larger animals in spite of the difference which might have been expected amongst the animal species. In this connection, a substantially larger amount of an antibody may be obtained by using larger animals such as rabbit, sheep, goat, horse, cattle and the like than by using smaller animals such as mouse, rat, guinea pig and the like.

The process of this invention makes it possible to obtain a large number of clones capable of producing an antibody which is capable of specifically distinguishing an antigen from other cross-reactive antigens. As a result of increased productivity of the specific antibody-producing clone, it may be practically possible to separate and isolate a specific clone. It was previously known in the literature that the probability of separating out and isolating a clone capable of recognizing a specified antigen was approximately $1/10^6$ to $1/10^7$. This means that such separation and isolation were practically impossible in the art. By the process of this invention, it is thus possible to obtain specific antibody-producing clones capable of discriminating specifically between a desired antigenic determinants and structurally related antigenic determinants even by immunization with an antigen containing cross-reactive determinants. The process of this invention renders it possible to obtain such specific antibodies at higher probability, and accordingly, it is also possible to increase the probability of producing such specific antibody-producing clones.

The process of this invention may be applied to any and all antibody-producing methods by modifying the method of coupling D-GL with a cross-reactive antigen, the typs of the coupling product and the like.

According to still further feature of this invention, there is provided a simple method for determining a certain substance, of which amount contained in the sample is unknown, by use of an antibody or antiserum obtained by the process as hereinafter described.

The following non-limiting examples illustrate the invention, in which the reagents and assay method used are as follows:

(1) Synthesis of DHT-3-(o-carboxymethyl)oxime and Te-3-(o-carboxymethyl)oxime [hereinafter referred to as DHT-3-CMO and Te-3-CMO, respectively] was effected by Erlanger et al method [J. Biol. Chem., 234: 1090 (1969)].

(2) Synthesis of hapten-D-GL:
(A) Synthesis of DHT-3-(o-carboxymethyl)oxime-D-GL [hereinafter referred to as DHT-3-D-GL]:
Prepared by Erlanger et al method [J. Biol. Chem., 228, 713 (1957)] using the following materials:

| | |
|---|---|
| DHT-3-CMO containing DHT-3-CMO labelled with $^3$H tracer | 20 mg |
| Dioxane (dried) | 6 ml |
| Tri-n-butylamine | 20 μl |
| Isobutyl chloroformate | 10 μl |
| Distilled water | 6 ml |
| D-GL (molecular weight = 49,000) | 30 mg |
| 1 N—NaOH | 150 μl |

The number of moles of DHT combined with 1 mole of D-GL was determined by measuring the radioactivity of 1 mg of $^3$H-DHT-3-CMO used as the tracer and the radioactivity per 1 mg of the reaction product. The molar ratio of DHT to D-GL in the reaction product was 30:1.

When the amounts of the water and dioxane used were equal to the corresponding amounts calculated on the basis of the mixed anhydride method by Erlanger et al [J. Biol. Che., 228, 713 (1957)], the mixture became gelatinized. Thus, large amounts of water and dioxane were added to the mixture in order to avoid gelatinization of the D-GL therein and moreover to effect the reaction adequately. Thus, conjugation of the D-GL with oxime was effected by the mixed anhydride method so that a sufficient amount of the oxime was combined with the D-GL.

(B) Preparation of testosterone-3-(o-carboxymethyl)oxime-D-GL (hereinafter referred to as Te-3-D-GL):
The same procedure as above was effected except the use of Te-3-oxime containing $^3$H-labelled Te-3-oxime as a tracer to obtain Te-3-D-GL (the molar ratio of Te:D-GL=30:1).

(3) Synthesis of hapten-KLH:
DHT-3-CMO-KLH (hereinafter referred to as DHT-3-KLH) and Te-3-CMO-KLH (hereinafter referred to as Te-3-KLH) were prepared by Erlanger et al method (ibid.). The molar ratios of DHT:KLH and Te:KLH of the product were 10:1 and 8:1, respectively.

(4) Radioimmunoassay:
Reagents used:
(1) $^3$H-Te standard solution was prepared by diluting 1,2-$^3$H-Te (58 Ci/m mol) with ethanol to give a concentration of 20,000 dpm/10 μl (45 pg as Te).
(2) $^3$H-DHT standard solution was prepared by diluting 5α-dihydro-1,2,4,5,6,7-$^3$H-Te (114 Ci/m mol) with ethanol to give a concentration of 40,000 dpm/10 μl (45 pg as DHT).
(3) 0.05M tris-buffer solution (pH=8.0) containing 0.05% BSA and 0.1% bovine serum γ-globulin (hereinafter referred to as BGG).
(4) Saturated ammonium sulfate solution.
(5) Unlabelled Te standard solution.
(6) Unlebelled DHT standard solution.

PROCEDURE 1

Determination of the anti-Te antibody titre:
A $^3$H-Te standard solution (10 μl) was put in a glass tube and dried by evaporation of the solvent, to which was added an antiserum (0.2 ml; diluted stepwise with a tris-buffer solution) and well mixed. The mixture was allowed to stand at room temperature for 2 hours, to which a saturated ammonium sulfate solution (0.2 ml) was added. The solution was well stirred and centrifuged (3000 r.p.m./20 minutes) to give a supernatant, of which 0.2 ml was put in a counting vial. The radioactivity of the sample was determined after addition of a scintillator [(2 ml; prepared by dissolving 2 g of 2,5-diphenyloxazole (PPO) in toluene (one liter).

PROCEDURE 2

Determination of the cross-reactivity of the anti-Te antibody with DHT:
Ten μl of a $^3$H-Te standard solution was put into a glass tube and divided into two groups. Unlabelled standard solutions of Te and DHT were respectively added to the tubes containing $^3$H-Te standard solutions to two groups. However, the amount of the unlabelled steriods added was stepwise increased on each occasion. All of the mixed solutions were dried by evaporation and 0.2 ml of antiserum was added to each tube and well mixed. Antiserum was used at the dilution which gave 60% of the $^3$H-Te (45 pg).

PROCEDURE 3

Determination of the titre of the anti-DHT antibody:
The same procedure as Procedure 1 was performed using $^3$H-DHT instead of $^3$H-Te.

PROCEDURE 4

Determination of the cross-reactivity of anti-DHT antibody with Te:

The same procedure as Procedure 2 was performed using $^3$H-DHT instead of $^3$H-Te.

EXAMPLE 1

Preparation of anti-Te specific antibody having low cross-reactivity (mouse):

Three groups of mice [each group consisting of 4–5 female mice; C57BL/6 strain; 8–10 weeks old] were used as test animals. Each mouse of the first group (control group) was administered with a saline solution alone. 3 days before primary immunization with Te-3-KLH, the mice of the second group were administered with DHT-3-D-GL (each 500 μg). All of the mice were administered with Te-3-KLH (100 μg/mouse) in saline together with complete Freund's adjuvant by injection (ip.). 3 weeks after this, Te-3-KLH in saline together with incomplete Freund's adjuvant was administered to all mice in the same amount by injection (ip.). 5, 7, 9 and 11 weeks after this, the same amount of Te-3-KLH in saline was administered to all mice by injection (ip.). 3 days before the 2nd immunization, and 3 days before the tertiary immunization i.e. 5 weeks after the primary immunization with Te-3-KLH, each mouse of the 3rd group was administered with DHT-D-GL (each 500 μg).

On each occasion, serum was collected from retroorbital plexus of the mouse successively at two weeks interval to investigate the titre and cross-reactivity of the antibody. The cross-reactivity was measured by Abraham's method [Abraham G. E., J. Clin. Endocr., vol. 29, 866–870 (1969)]. The results are shown in the following Table 1.

TABLE 1

(A) Titre of anti-testosterone antibody\*, and
(B) its cross-reactivity with DHT\*\*

| Weeks | | Group 1 (not pre-treated) | Group 2 pre-treated with DHT-3-D-GL (500 μg, ip.) | Group 3 (not pre-treated)\*\*\*\* |
|---|---|---|---|---|
| 9 | A | 3331 | 1004\*\*\* | Formation of |
|   | B | 30.3 ± 4.9 | 7.1 ± 1.9\*\*\* | antibody: ± |
| 11 | A | 4320 | 1711 | Formation of |
|    | B | 54.1 ± 24.1 | 11.2 ± 6.2 | antibody: ± |
| 13 | A | 2886 | 819 | Formation of |
|    | B | 43.0 ± 12.5 | 7.9 ± 4.5 | antibody: ± |
| 19 | A | 1494 | 461 | Formation of |
|    | B | 30.8 ± 10.1 | 7.4 ± 4.1 | antibody: ± |

Notes:
\*Titre is expressed by the reciprocal number of the dilution of the serum capable of binding 50% of $^3$H—testosterone (45 pg).
\*\*Cross-reactivity (%) is expressed by [amount (ng) of testosterone needed to inhibit binding by 50%/amount (ng) of DHT needed to inhibit binding by 50%] × 100%.
\*\*\*Mean value of antibody titre is expressed by the geometric mean, and cross-reactivity is expressed by the arithmetic mean ± standard deviation.
\*\*\*\*DHT-3-D-GL was not used for pretreatment, but was administered after the primary immunization.

As is apparent from this table, the antibody titre of the second group was slightly lower than that of the first (control) group, and the kinetics of antibody formation of the second group was similar to that of the control group. On the other hand, in the third group no significant antibody formation was observed throughout the entire period. The cross-reactivity with DHT of the second group which was pretreated with DHT-3-D-GL was substantially lower than that of the control group.

The relationship between the antibody titre and cross-reactivity of the antibody obtained from each of the test mice was plotted. However, although the data are not shown here, no significant relationship between the antibody titre and cross-reactivity was found. In general, it was found that the treatment with DHT-3-D-GL results in a decrease in cross-reactivity with DHT and this was not correlated with a decrease in the antibody titre. In other words, a decrease in the cross-reactivity did not result in a significant decrease in titre.

From these facts, it is postulated that, when clones having a cross-reactivity with DHT are removed by pretreatment with DHT-3-D-GL, subsequent immunization with Te-3-KLH may selectively enhance the formation of antibody-forming clones having a higher specificity with respect to Te. The formation of antibodies having a low cross-reactivity according to the method of this invention is an important advantage as described hereinbefore.

EXAMPLE 2

Preparation of a specific anti-DHT antibody having low cross-reactivity (mouse):

Five groups of mice (each group consisting of 5–7 female mice; C57BL/6 strain; 8 weeks old) were used in this Example. Mice of the first group (control group) were not treated with Te-3-D-GL and the primary immunization was effected using DHT-3-KLH. Three and 5 weeks respectively after this, the secondary and tertiary immunizations were effected, followed by additional immunization treatments which were effected at 2 weeks intervals. Mice of other groups were also immunized in this manner simultaneously with the mice of the control group.

Three days before the primary immunization with DHT-3-KLH, Te-3-D-GL (500 μg/mouse) was administered to the mice of the second group by injection (ip.). As another control group, mice of the third group were treated with DHT-3-D-GL (500 μg/mice) by i.p. injection, 3 days before the primary immunization with DHT-3-KLH.

Three days before the secondary immunization which was effected 3 weeks after the primary immunization using DHT-3-KLH, Te-3-D-GL and DHT-3-D-GL (each 500 μg/mouse) were respectively administered (ip.) to the mice of the 4th and 5th groups. From 7 weeks after the primary immunization, serum was collected from each of the mice of 5 groups at 2 week intervals to determine the antibody titre and cross-reactivity. The results obtained by using the serum collected 13 weeks after the primary immunization are shown in Table 2.

TABLE 2

| Group | Antibody titre\* | Cross-reactivity\*\* |
|---|---|---|
| 1 | 3457 | 90.3 ± 12.9 |
| 2 | 1286 | 38.2 ± 14.6 |
| 3 | 1079 | 86.3 ± 23.7 |
| 4 | 0 | |
| 5 | 0 | |

\*1 and \*2: Cf. footnote of Table 1

Table 2 indicates that anti-DHT antibody having a low cross-reactivity was obtained by pre-treatment with Te-3-D-GL (the second group). In this example, no significant formation of anti-DHT antibody was observed in the 4th and 5th groups which had been treated with Te-3-D-GL or DHT-3-D-GL after the primary immunization.

In the 3-rd group, the mice were pre-treated with DHT-3-D-GL and were then immunized with DHT-3-KLH, the thus-formed anti-DHT antibody showed a high cross-reactivity with Te as in the case of the control mice and almost the same magnitude of antibody titre was observed in the 2nd and 3rd groups. From these results, it can be concluded that an anti-DHT antibody having a low cross-reactivity with Te was obtained by treatment with Te-3-D-GL.

EXAMPLE 3

Preparation of anti-DHT or anti-Te antibody (rabbit):

Six groups of female rabbits (each group consisting of 2 rabbits; weight about 3 kg) were used.

Te-3-D-GL (10 mg/rabbit) was administered (ip.) to the rabbits of the first group three days before primary immunization with 100 μg of DHT-3-KLH emulsified in complete Freund's adjuvant, and 3 weeks after this, the rabbits were given subcutaneously a secondary immunization with 200 μg of DHT-3-KLH in incomplete Freund's adjuvant.

They were then consecutively boosted subcutaneously four times with 200 μg of DHT-3-KLH in complete Freund's adjuvant and incomplete Freund's adjuvant alternately at monthly intervals.

The control rabbits (the 2nd group) were also immunized with DHT-3-KLH in a similar manner to that applied to the first group. However, Te-3-D-GL was not given to them. The rabbits of the 3rd group were treated with (ip.) Te-3-D-GL (10 mg/rabbit) 3 days before the secondary and tertiary immunizations with DHT-3-KLH, which were effected 3 and 7 weeks respectively after the primary immunization.

The rabbits of the 4th group were treated (ip.) with DHT-3-D-GL (10 mg/rabbit) 3 days before the primary immunization with Te-3-KLH. The method of immunization with Te-3-KLH was effected in a similar manner to that used for the first group.

In the 5th group (control group), the rabbits were immunized with Te-3-KLH in a similar manner to that used for the 4th group. However, no DHT-3-D-GL was administered to them.

In the 6th group, the rabbits were treated (ip.) with DHT-3-D-GL (10 mg/rabbit) 3 days before the secondary and tertiary immunizations with Te-3-KLH (effected 3 and 7 weeks after the primary immunization, respectively).

Ten days after the above-mentioned booster injection procedures, serum was collected from each rabbit and determined to give the following results.

In the 3rd and 6th groups, no significant formation of the antibody was observed throughout the entire period. Anti-DHT and anti-Te-antibodies obtained respectively from the 2nd and 5th groups (control groups) showed substantially the same reactivity on both the hapten used for immunization and the cross-reactive hapten. That is, the anti-DHT antibodies of the rabbits of the 2nd group showed a 100% cross-reactivity with Te and the anti-Te antibodies of rabbits of the 5th group showed a 95.2% cross-reactivity with DHT. On the other hand, the rabbits of the first and 4th groups gave significantly low cross-reactivities, and the anti-DHT antibodies from the rabbits of the first group showed a 11.9% cross-reactivity with Te and the anti-Te antibodies from the rabbits of the 4th group showed a 22.0% cross-reactivity with DHT.

EXAMPLE 4

Determination of Te and DHT in human blood using specific anti-Te and anti-DHT antibodies obtained from the rabbit:

(1) Anti-Te and anti-DHT antibodies having low cross-reactivity were obtained from the rabbits of groups 1 and 4 of the above-mentioned Examples. The following tests were effected to investigate the practical feasibility of using these antibodies for determining the Te and DHT present in human serum.

For this purpose, given amounts of Te and DHT were respectively added to samples of human serum, and the relationship between the added amount and the amount of Te or DHT which was determined by radioimmunoassay using the said antiserum was investigated. In order to determine the level of Te present in human serum, Te (1, 2 and 4 ng) or DHT (0.1; 0.2; and 0.3 ng) was added to a pooled serum (1 ml; collected from female and having a low Te value), to which $^3$H-Te (200 dpm) or $^3$H-DHT (2000 dpm) was then added in order to determine the recovery effected in the extraction step. On each occasion, the mixture was well mixed and a mixture of hexane/ether (3:2; 3 ml) added, followed by shaking for one minute with a vortex mixer. After this, the test tube was allowed to stand in a dry ice/acetone bath for 10 seconds and the organic solvent layer transferred to another test tube. The organic solvent was evaporated off and the residue was dissolved with ethanol (2 ml) with shaking. A part of the ethanol solution was put into a small test tube. The amount of the solution transferred to the test tube was adjusted so as to enable the determination of Te from the inhibition curve calibrated by using the above-mentioned antiserum. The solution was dried by evaporation and subjected to radioimmunoassay using the low cross-reacting anti-Te antibody which was obtained by DHT-3-D-GL treatment. On the other hand, an ethanol solution (0.5 ml) was put in a vial and dried by evaporation. Then a scintillator was added to the residue and counted to determine the recovery in the extraction step. This recovery ratio was used to correct the value obtained by the radioimmunoassay.

In order to determine the level of DHT present in the serum, DHT (0.2 and 0.5 ng) or Te (0.2 and 0.5 ng) was added to the pooled serum (1 ml) obtained from female humans, to which was then added $^3$H-Te or $^3$H-DHT (2000 dpm) to determine the recovery. Hexane/ether (3:2, 3 ml) was added to the mixture and extracted in a similar manner to that described above. Ethanol (2 ml) was added to the residue of the extract and a part of the ethanol solution was put into a small test tube. The amount of the solution in the test tube was adjusted to be sufficient to enable the determination of DHT using the inhibition curve of DHT obtained by using the above-mentioned antiserum. The solution was dried by evaporation and subjected to radioimmunoassay using the antiserum of low cross-reactivity which was obtained by the treatment with Te-D-GL. On the other hand, the ethanol solution (0.5 ml) was put into a vial and ethanol was removed by evaporation. To the residue was added the scintillator and counting was effected to determine the recovery in the extracting step. This recovery ratio was used to correct the value obtained by the radioimmunoassay.

As a result, it was found that when an anti-Te antibody having low cross-reactivity was used to measure added Te (1,2 and 4 ng) of normal female human serum originally having a Te value of 0.30 ng, the measured Te value was 1.15, 2.30 and 4.60 ng, respectively.

On the other hand, when DHT (0.1, 0.2 and 0.3 ng) was added to the female human serum instead of Te, in order to investigate the influence of DHT upon the amount of Te assayed, no significant influence was found and the level of Te in the normal female human serum was almost unchanged.

In a separate experiment, DHT (0.2 and 0.5 ng) was added to the normal female human serum and the amount of DHT in the serum was determined by the use of an anti-DHT antibody having low cross-reactivity. It was found that the amount of DHT in the normal female human serum before addition was 0.21 ng, then changed after addition to 0.41 and 0.72 ng, respectively after addition in each occasion. These values were sufficiently in conformity with the added amounts of DHT.

On the other hand, when Te (0.2 and 0.5 ng) was added to the normal female human serum instead of DHT to investigate the influence of Te upon the level of DHT assayed, no significant change of the DHT level in the normal female human serum was made by addition of Te.

It is apparent that Te and DHT levels in the serum can be exactly determined by using the antibodies having low cross-reactivity described in Example 3.

(2) Assay of a sample containing a mixture of specific antigen and cross-reacting antigen:

The DHT level in human blood was again determined by using a low cross-reactive anti-DHT antibody originating from rabbits, as described above. On each occasion, DHT and Te (5 and 10 ng; 10 and 5 ng; or 10 and 10 ng, respectively) (0.1 m) were simultaneously added to female human pooled serum and the determination was effected in a similar manner to that described in (1) above. As a result, it was found that, as shown in Table 3, even when a large amount of Te, i.e. a cross-reactive antigen is present in the sample, the amounts of DHT were 5.67, 10.17 and 9.20 ng on each occasion. Thus it can be said that DHT may be assayed accurately by the use of the low cross-reactive anti-DHT antibody obtained in Example 3, even when a large amount of Te which is the cross-reactive antigen is present in the sample.

TABLE 3

| Amount of DHT added (ng) | Amount of Te added (ng) | DHT Found (ng) |
|---|---|---|
| 5 | 10 | 5.67 |
| 10 | 5 | 10.17 |
| 10 | 10 | 9.20 |

Similarly, Te and DHT (respectively 5 and 10 ng; 10 and 5 ng or 10 and 10 ng) were added to the serum (0.1 ml) and Te levels were determined by using the low cross-reactive anti-T antibody. In each case, the amounts of Te found were 6.80, 10.3 and 10.5 ng, respectively, as shown in Table 4, from which it is apparent that when above mentioned anti-Te antibody of low cross-reactivity is used, Te is accurately assayed in the presence of DHT which serves as a cross-reactive antigen.

TABLE 4

| Amount of Te added (ng) | Amount of DHT added (ng) | Te found (ng) |
|---|---|---|
| 5 | 10 | 6.80 |
| 10 | 5 | 10.3 |
| 10 | 10 | 10.59 |

(3) Assay of human sample (direct method):

The term "direct method" denotes the assay method which does not require prior separation of Te and DHT. For comparison, the values obtained by a conventional method are also indicated. In the latter method, Te and DHT are separated by paper chromatography prior to determination.

(3.1) Assay of Te in human serum:

(A) Preparation of samples:

Male human serum (each 0.1 ml) and female human serum (each 0.5 ml) were put into test tubes, respectively, and $^3$H-Te (each 3000 dpm) added in order to determine the recovery in the extraction step or extraction-chromatography step. Distilled water (each 0.5 ml) was added to the male human serum. A mixture of hexane/ether (3:2, each 3 ml) was added to the serum samples and well mixed by using a vortex mixer for one minute. The test tubes were then put into a dry-ice/acetone bath for 10 seconds to freeze the serum fractions. The organic solvent layer was transferred to another test tube and the organic solvent was removed by evaporation.

(B) Direct method:

Ethanol (0.4 ml) was added to each residue of the male human serum samples and well mixed, and the solution was transferred into a radioimmunoassay tube. The amount of the solution in the test tube was adjusted to fall into a range of 50 to 400 pg, that is, 100 μl in the case of normal range and 50 μl in the case of the serum of high Te level such as Test Nos. 1, 2 and 3 in Table 5 described hereinafter. In order to determine the recovery in the extraction step, the solution (100 μl) was transferred into a vial and dried by evaporation. After addition of a scintillator, the residue was counted.

In the case of female human serum, ethanol (0.7 ml) was added to each residue, and the ethanol solution (0.5 ml) transferred to a radioimmunoassay tube. In order to determine the recovery in the extraction step, the solution (100 μl) was put into a vial and dried by evaporation. The residue was counted after addition of a scintillator.

In both cases, ethanol was removed by evaporation under a nitrogen stream, and the dried extract obtained was used for radioimmunoassay.

(C) Paper chromatography:

The dried extract prepared in a similar manner to that described above in (A) was applied to a paper with three 50 μl rinses of chloroform. On an identical strip of paper, Te (10 μg) was applied as a reference marker and run with each set of determinations. The paper strips were set in a chromatograph tank containing Bush A (a solvent system of cyclohexane/methanol/water=10:8:2). After 2 hours for equilibration, they were developed in the upper layer of Bush A.

After developing for 16 hours, the spot of Te used as a reference was detected by ultraviolet absorption at 254 nm and a 3 cm long section of the test paper corresponding to the location of the said spot of reference marker was cut off from the paper and extracted with ethanol (3 ml). Ethanol was removed by evaporation under a nitrogen stream, and the residue was used for radioimmunoassay in a similar manner to that described in the direct method.

(D) Radioimmunoassay:

In order to prepare a Te standard curve, ethanol solution containing 0, 20, 50, 100, 200 or 400 pg of Te was put into test tube in duplicate. On each occasion, an ethanol solution (each 10 μl) containing 20,000 dpm of $^3$H-Te/10 μl was added to the test tube and then ethanol was removed by evaporation. An anti-Te antiserum originating from the rabbit was diluted with a 0.05M tris-buffer solution [pH=8.0; containing 0.05% BSA and 0.1% BGG] to the concentration ($B_0$=60%) which is capable of binding 60% of 20,000 dpm of $^3$H-Te (45 pg as Te), and 0.2 ml of this antiserum solution was put into each test tube, followed by mixing by the use of a vortex mixer. Separately, this tris-buffer solution (each 0.2 ml) was transferred to two test tubes, each containing 20,000 dpm of $^3$H-Te alone, and well mixed to obtain a total dpm ($B_0$=100%). After standing at room temperature for 2 hours, saturated ammonium sulfate (0.2 ml) was added to the solution and well mixed. Centrifugation was then effected at 3000 rpm for 10 minutes, and 0.2 ml of the supernatant was then transferred into a vial. After addition of a scintillator (0.2 ml), the activity was counted and calculated to a $B/B_0$ (%).

(3.2) Assay of DHT in the female human serum:

Sampling of serum, extraction and separation of DHT and Te by paper chromatography were conducted in the same manner as for the assay of Te except for using a female human serum sample. The location of a reference DHT marker was detected by spraying with a solution of equal volumes of a 1% absolute ethanol solution of m-dinitrobenzene and 2.5N sodium hydroxide in absolute ethanol. Radioimmunoassay of DHT was effected by the use of the standard ethanol solution of DHT and an ethanol solution of $^3$H-DHT (40,000 dpm/10 μl) in a similar manner to that used for radioimmunoassay of Te. In both direct and conventional paper chloromatography methods, the result from the radioimmunoassay was corrected by the recovery ratio.

In the direct method, the recovery ratio of Te or DHT was within a range of 95 to 100%, and therefore the recovery correction by the addition of $^3$H-Te or $^3$H-DHT may not be needed for routine work.

The results are shown in Tables 5 and 6.

(E) Results and analysis:

TABLE 5

| Test No. | Serum used (*male; **female) | Amount of Te found (ng/ml) | |
|---|---|---|---|
| | | Direct method | Paper chromatography |
| 1 | * | 10.35 | 9.60 |
| 2 | * | 13.34 | 15.36 |
| 3 | * | 22.84 | 19.08 |
| 4 | * | 8.92 | 9.16 |
| 5 | * | 4.40 | 4.38 |
| 6 | * | 5.00 | 4.90 |
| 7 | * | 8.20 | 7.95 |
| 8 | * | 7.43 | 7.10 |
| 9 | ** | 0.88 | 0.740 |
| 10 | ** | 0.310 | 0.292 |
| 11 | ** | 0.180 | 0.191 |
| 12 | ** | 0.160 | 0.158 |
| 13 | ** | 0.340 | 0.356 |
| 14 | ** | 0.500 | 0.490 |
| 15 | ** | 0.250 | 0.240 |
| 16 | ** | 0.154 | 0.218 |

It is apparent from this table that the results from two assay methods are substantially in conformity with each other.

TABLE 6

| | (Serum used - serum from female human) | |
|---|---|---|
| | DHT found (ng/ml) | |
| Test No. | Direct method | Paper chromatography |
| 1 | 0.175 | 0.154 |
| 2 | 0.210 | 0.201 |
| 3 | 0.198 | 0.200 |
| 4 | 0.195 | 0.190 |
| 5 | 0.280 | 0.280 |
| 6 | 0.250 | 0.260 |
| 7 | 0.221 | 0.232 |
| 8 | 0.201 | 0.198 |

In this table, the results from two methods are substantially in conformity with each other.

As apparent from these experimental results, it is possible by the direct method of this invention using a low cross-reactive antibody, to assay simply and accurately the desired substance even in the presence of a cross-reacting antigen. In this case, it is no longer necessary to separate out the cross-reacting antigen, prior to assay, by paper chromatography as used in conventional methods.

In the process of this invention a specific antibody as well as a clone capable of producing such an antibody may be obtained by pre-treatment of an animal with a conjugate of a cross-reactive antigen and D-GL so as to induce an immunological unresponsiveness to a cross-reactive antigen. The present invention is not, of course, restricted to the above-mentioned specific embodiments using Te-3-D-GL and DHT-3-D-GL, and may be applied in a wide variety of cases, such as exemplified by Example 5 hereinafter, in which substantially the same results were obtained even when Te and DHT were coupled to the carriers at a different site. In the following example, Te and DHT were again used as model systems and their coupling site was changed from the 3rd to the 15th position, so that the structure of the hapten exposed on the surface of carrier molecules was changed.

EXAMPLE 5

Properties of an antiserum obtained by using a conjugate of 15β-carboxyethylmercaptotestosterone (hereinafter referred to as 15β-CEM-Te) and 15β-carboxyethylmercapto-5α-dihydrotestosterone (hereinafter referred to as 15β-CEM-5α-DHT) with KLH and D-GL:

In this example, 15β-CEM-Te was synthesized by the method reported by Rao, P. N. et al: [Steroid, 28, p. 101 (1976)] and 15β-CEM-5α-DHT was synthesized by the method reported by Rao, P. N., et al: [Steroid, 29, p. 171 (1977)].

The conjugation of 15β-CEM-Te to D-GL and KLH and the conjugation of 15β-CEM-5α-DHT to D-GL and KLH were performed in a similar manner to that used for the above-mentioned conjugation of DHT-3-CMO or Te-3-CMO to D-GL or KLH. The conjugate thus obtained are referred to as Te-15-D-GL, Te-15-KLH, DHT-15-D-GL and DHT-15-KLH, respectively.

In this example, 6 groups of mice (each group consisting of 7 mice; C57BL/6 strain; 8–10 weeks old) were used.

Te-15-KLH (100 μg/mouse) was used for immunization. The first group (control group) was administered with a saline solution alone. 3 days before the primary immunization, the mice of the second group and third group (another control group) were respectively administered with DHT-15-D-GL and Te-15-D-GL (each 500 μg/mouse) by injection (ip.). 3 weeks after the primary immunization, the secondary immunization of the first to the third groups was effected. Every 2 weeks after this, additional booster immunizations were effected. The 4th to the 6th groups were immunized with DHT-15-KLH. 3 days before the primary immunization, Te-15-D-GL (500 μg/mouse) was administered (ip.) to the mice of the fifth group. Simultaneously with the 5th group, the mice of the 4th group served as a control group and saline instead of Te-15-D-GL was administered to this group. DHT-15-D-GL (500 μg/mouse) was administered (i.p.) to the mice of the 6th group (another control group) 3 days before primary immunization with DHT-15-KLH.

Seven weeks after primary immunization, serum was collected from each mouse at 2 week intervals in order to measure the antibody titre and cross-reactivity. The antiserum obtained 13 weeks after primary immunization had the highest antibody titre, from which the following results were obtained.

Properties of anti-Te antisera from the first, second and third groups:

When expressed by the reciprocal of the dilution of antiserum capable of binding 50% of $^3$H-Te (45 pg), the anti-Te antibody titres of the mice of the first (control) and second groups are within the ranges of 1,600 to 9,000 and 1,000 to 3,500, respectively, and the mice of the third group which had been given Te-15-D-GL showed no formation of the antibody.

When determined by Abraham's method, the antiserum from the mice of the first group showed cross-reactivities within a range of from 4.1 to 8.2, whereas cross-reactivities of from 0.27 to 0.94 were obtained in the antiserum from the mice of the second group. The results of the 2nd group are superior to the cross-reactivities with DHT obtained by any other anti-Te antisera reported by others. Thus it can be said that the cross-reactivity with DHT of the obtained antiserum was practically negligible according to the present invention. It is known that 1.81% is the lowest cross-reactivity of any anti-Te antiserum reported in the literature in so far as DHT is concerned and that Rao et al obtained this low value by the use of anti-Te antiserum prepared by immunizing rabbits with 15β-CEM-Te-BSA*[P. N. Rao et al: Steroid, 28 p. 101 (1976)] which is also used in the above-mentioned example. The cross-reactivities of the mice of the first group in this example are substantially equivalent to this lowest value [* BSA=bovine serum albumin].

Properties of anti-DHT antisera from the 4th, 5th and 6th groups:

When expressed by the reciprocal of the dilution capable of binding 50% $^3$H-DHT (45 pg), the anti-DHT antibody titres of the 4th group (control group) were within a range of from 1,500 to 5,600 and the corresponding value of the 5th group to which Te-15-D-GL was administered were from 1,000 to 7,600. The mice of the 6th group to which DHT-15-D-GL was administered showed no formation of antibodies.

When the antisera obtained from the mice of the 5th group, which had been treated with Te-15-D-GL, were investigated by Abraham's method, the cross-reactivities with Te of the thus-obtained antisera were within a range from 6.5 to 19.0% in contrast to the cross-reactive values of from 48.3 to 68.5 in antisera from the mice of the 4th group (control group). These facts indicate that the administration of Te-15-D-GL significantly reduced the cross-reactivity with Te.

No formation of antibodies was found in the mice of the 6th group to which DHT-15-D-GL was administered. The reason therefore is believed to be the specific inactivation of anti-DHT antibody-producing clones by administration of DHT-D-GL.

Remarks on the undergoing examples:

The reagents and assay method used in the undergoing examples are explained as follows: In these Examples, the invention is applied to peptide determinants.

(R1) Preparation of pentagastrin-D-GL conjugate Reference: Liu et al, Biochemistry, vol. 18, 690 (1979)

(R1A) Synthesis of S-acetylmercaptosuccinyl-D-GL (hereinafter referred to as Ac-S-D-GL):

D-GL (Mw=34,300; 40 mg=1.166 μmol) was dissolved in a 0.125M phosphate buffer solution (900 μl; pH=7.2) and the pH was adjusted to 7.2 with 1N NaOH solution. After the addition of 50 μl (57.44 μmol) of a dimethylformamide solution (hereinafter referred to as DMF) of S-acetylmercaptosuccinic anhydride (200 mg/ml), the mixture was stirred at room temperature for 30 minutes. During the reaction, the pH of the mixture was kept at 7.2. After completion of reaction, the solution was applied to a Sephadex G-25 column, equilibrated with 0.01M phosphate buffer saline (pH=7.2) containing 0.01M Na$_2$-EDTA so as to separate the reaction product from unreacted S-acetylmercaptosuccinic anhydride. A fraction (100 μl) of the solution containing the reaction product was added with an aqueous solution of 0.5M hydroxylamine (100 μl=50 μmol; pH=7.3) and incubated at 37° C. for 20 minutes to remove the protecting acetyl group. The numbers of sulfhydryl groups introduced in D-GL were determined by the method of Ellman et al [Arch. Biochem. Biophys., vol. 82, p. 70 (1959)] in the following manner. The reaction solution (50 μl) was added to a methanol solution of 0.01M 5,5'-dithiobis-(2-nitrobenzoic acid) (deoxidized; 0.1 ml) and 1 ml of tris-buffer solution (pH=8.0) and reacted for 20 minutes, and the absorbance at 412 nm was measured. The number of S-acetylmercapto groups introduced into D-GL was about 15/molecule. The thus-obtained S-acetyl-mercaptosuccinyl-D-GL was hereinafter referred to as Ac-S$_{15}$-D-GL. The yield was approximately 77%. As D-GL has no absorbance at 280 nm, it was not possible to measure the recovery of the fraction containing the D-GL derivative by the absorbance at 280 nm. The recovery was therefore determined by using, as monitoring substance, a reaction product which was obtained by the reaction of N-succinimidyl-3-(4-hydroxyphenyl)propionate and D-GL, and applied to a column of Sephadex G-25. As this product does have an absorbance at 280 nm, the determination was conveniently measured by the absorbance at 280 nm.

(R1B) Preparation of m-maleimidobenzoyl-pentagastrin (hereinafter referred to as MB-pentagastrin):

Pentagastrin (11 mg; 16.1 μmol) was dissolved in 0.1M phosphate buffer (9.5 ml; pH=8.0) and was then added in one portion to m-maleimidobenzoyl-N-hydroxy-succinimide ester (25.3 mg, 80.5 μmol; hereinafter referred to as MBS) dissolved in DMF (one ml). The mixture was stirred, and the reaction was monitored by thin layer chromatography using a solvent system of cyclohexane/ethyl acetate=1:1 by volume. Twenty-five minutes after the beginning of the reaction, dichloromethane (3 ml) was added to the reaction mixture to remove unreacted MBS. The mixture was well agitated and centrifuged.

The upper layer of the buffer solution was put into another test tube. The dichloromethane layer (lower layer) was treated with a small amount of a phosphate buffer, well mixed and centrifuged. The upper layer was combined with the said solution. By thin layer chromatography, it was confirmed that the unreacted MBS was almost completely removed from the fraction of the buffer solution containing MB-pentagastrin.

Separately, the above-mentioned buffer solution (20 $\mu$l) containing MBS-pentagastrin was added to an aqueous solution of 2-mercaptoethanol (20 $\mu$l; 70 n mol; deoxidized with nitrogen stream). The reaction was effected at room temperature for 20 minutes, and the molar quantity of 2-mercaptoethanol consumed was determined by Ellman's method, which correspond to the quantity of maleimidobenzoyl group introduced into pentagastrin. The number of maleimidobenzoyl group introduced into one molecule of pentagastrin was 0.9. This compound was hereinafter referred to as $MB_{0.9}$-pentagastrin.

(R1C) Preparation of a conjugate of pentagastrin and D-GL;

A solution of $Ac-S_{15}$-D-GL prepared in R1A and a solution of $MB_{0.9}$-pentagastrin prepared in R1B were mixed together to effect the reaction in the following manner. After complete deoxidation in a nitrogen stream, a 5M aqueous solution of hydroxylamine (500 $\mu$l; pH=7.3) was added to the mixture and the mixture stirred at room temperature for one hour. Then part of the reaction solution was removed to investigate the presence of unreacted groups. None of such groups was found. That is, there were no SH groups which had not bound with MB-pentagastrin. Thus, it was confirmed that all of the SH groups held by D-GL had reacted with MB-pentagastrin.

Two hours after addition of the aqueous solution of hydroxylamine, 2-mercaptoethanol was added to the reaction mixture to give a final concentration of 1 mM, followed by stirring for 20 minutes. After this, the reaction mixture was dialyzed against 0.01M phosphate buffer solution (pH=7.2) for about 24 hour using a cellulose membrane, and the thus-obtained solution was used with or without dilution.

The molar ratio of pentagastrin to D-GL in the thus-obtained pentagastrin-D-GL conjugate was 15:1. This product was hereinafter referred to as $pentagastrin_{15}$-D-GL.

(R2) Preparation of CCK-8-P-keyhole limpet hemocyanin (hereinafter referred to as CCK-8-P-KLH):

(R2A) Preparation of S-acetyl-mercaptosuccinyl-KLH (hereinafter referred to as Ac-S-KLH):

Prepared in a similar manner to that used for the preparation of Ac-S-D-GL as described in R1A.

Prior to the synthesis, KLH (70 mg) was dissolved in a 1% solution of $K_2CO_3$ (1.4 ml) and dialyzed against a 0.125M phosphate buffer solution (pH=7.2) and the absorbance at 280 nm was measured so that the amount of KLH was determined.

S-acetylmercaptosuccinic anhydride (6.5 $\mu$mol) was added to the KLH solution of 0.7 ml containing 26.0 mg (corresponding to 260 nmol assuming that the molecular weight is about 100,000; pH=7.2), and the synthesis was effected in a similar manner to that described in R1A. The molar ratio of the S-acetylmercapto group to KLH in the product was 6.8 (hereinafter referred to as $Ac-S_{6.8}$-KLH).

(R2B) Preparation of m-maleimidobenzoyl-CCK-8-P (hereinafter referred to as MB-CCK-8-P):

Prepared in a similar manner to that used for the preparation of MB-pentagastrin. CCK-8-P (0.42 mg; 385 n mol) synthesized by the fragment condensation method was dissolved in 0.2M phosphate buffer (0.5 ml) and subjected to reaction with MBS (600 $\mu$g, 1.9 $\mu$mol) by using 50 $\mu$l of DMF solution. (1.2 mg MBS dissolved in 100 $\mu$l DMF). The reaction product contained CCK-8-P and MB in a ratio of 1:1.0 (hereinafter referred to as $MB_{1.0}$-CCK-8-P).

(R2C) CCK-8-P-KLH:

An $Ac-S_{6.8}$-KLH solution (2.3 ml; 75.9 n mol) prepared in R2A and an $MB_{1.0}$-CCK-8-P solution prepared in R2B were mixed together and 0.5M $NH_2OH$ (0.3 cc; 150 $\mu$mol) added. After this, an analogous treatment to that described in R1C was effected. The ratio of CCK-8-P to KLH in the resultant product was about 5:1.

(R3) CCK-8-P-bovine serum albumin (hereinafter referred to as CCK-8-P-BSA):

(R3A) Preparation of S-acetylmercaptosuccinyl-BSA:

Synthesized in a similar manner to that described in R1A using BSA (25 mg; 351 n mol) and S-acetylmercaptosuccinic anhydride (1.5 mg; 8.8 $\mu$mol). The ratio of BSA to S-acetylmercapto group in the product was 7.6:1.

(R3B) Preparation of MB-CCK-8-P:

CCK-8-P (0.5 mg; 457 nmol) was dissolved in 0.1M phosphate buffer solution (0.5 ml; pH=8.0) and subjected to the reaction with MBS (700 $\mu$g, 2.29 $\mu$mol) by using 50 $\mu$l of DMF solution (1.4 mg MSB dissolved in 100 $\mu$l DMF) in a similar manner to that described in R1B. The ratio of MB to CCK-8-P was 1.0:1. The product was referred to as $MB_{1.0}$-CCK-8-P hereinafter.

(R3C) Preparation of CCK-8-P-BSA:

The solution obtained in R3A (1.9 ml; 84 nmol) and the solution obtained from R3B were mixed together and added with $0.5M.NH_2OH$ (0.35 ml; 175 $\mu$mol). The mixture was treated in a similar manner to that described in R1C to obtain a conjugate, in which the ratio of CCK-8-P to BSA was about 5:1 (referred to as CCK-8-P-BSA hereinafter).

(R4) Preparation of pentagastrin-BSA (R4A) Preparation of MB-pentagastrin:

Pentagastrin (0.5 mg, 750 nmol) was dissolved in 0.1M phosphate buffer solution (0.5 ml; pH=8.0) and subjected to reaction with MBS (1.05 mg; 3.3 $\mu$mol) by the use of 50 $\mu$l of DMF solution prepared by dissolving MBS (2.1 mg) in DMF (100 $\mu$l). The reaction was effected in a similar manner to that described in R1B. The ratio of MB to pentagastrin was 1.0:1. The product was referred to as $MB_{1.0}$-pentagastrin hereinafter.

(R4B) Preparation of pentagastrin-BSA:

A solution (2.54 ml; 112 nmol) prepared in R3A was mixed with the solution prepared in R4A. 0.5M $NH_2OH$ (0.4 ml; 200 $\mu$mol) was added to the mixture and treated in a similar manner to that described in R1C. The ratio of pentagastrin to BSA in the product was about 5:1. The product obtained was referred to as $pentagastrin_5$-BSA.

(R5) A similar procedure to that described in the above-mentioned R1 was repeated except for the use of a D-GL having a molecular weight of 115,000 instead of one having a molecular weight of 34,300 (the molar reaction ratio being the same as that described in $R_1$).

Pentagastrin$_{33}$-D-GL was obtained having the same density as the antigen determinant combined with D-GL on the molecular surface.

EXAMPLE 6

(A) Schedule of immunization and collection of serum:

(C57BL/6J×DBA/2) F$_1$ female mice, each group consisting of 6 mice, were immunized.

All mice in each group were immunized with CCK-8-P-KLH (each 10 μg) in complete Freund's adjuvant (each 0.2 ml), and 3 weeks after this, they were further immunized with CCK-8-P-KLH (each 10 μg) in incomplete Freund's adjuvant (0.2 ml). Two weeks after the secondary immunization, additional booster immunizations with CCK-8-P-KLH (each 10 μg) mixed with 2 mg of aluminium hydroxide gel were effected. Two and 4 weeks after this, they were further immunized twice by injection of 0.2 ml of saline solution containing CCK-8-P-KLH (each 10 μg). All treatments were effected by i.p. injection.

Three days before primary immunization, 0.5 ml of saline solution of pentagastrin$_{15}$-D-GL (each 300 μg) was administered to all the mice of the second group. The mice of the first group served as the control and 0.5 ml of saline without pentagastrin$_{15}$-D-GL was administered to each mouse in this group.

Three days before the secondary immunization and 3 days before the tertiary immunization, 0.5 ml of saline solution of pentagastrin$_{15}$-D-GL (each 300 μg) was administered (i.p.) to all the mice of the 3rd group.

Blood was taken out from the retro-orbital plexus of each animal to prepare the antiserum.

(B) Assay of antibody titre:

Effected by radioimmunoassay. Each 100 μl of a 0.01M phosphate buffer solution (pH=7.2; containing 0.15M NaCl referred to as PBS, hereinafter) containing 10 μg/ml of an antigen (as CCK-8-P-BSA or pentagastrinBSA) was dispensed into each well of a polyvinyl-made round bottom microplate for solid phase radioimmunoassay and the antigen was bound to the surface of the polyvinyl plate by incubation at room temperature for 2 hours. The antigen solution in the well was discarded and the well was washed 4 times with tap water. After flicking off the excess water, 200 μl of 1% BSA saline was added to each well and allowed to stand at 4° C. overnight so that the protein-combining ability of the polyvinyl plate was completely quenched. After this, the solution was removed from the wells and the plate rinsed with tap water 4 times. The plate was used for radioimmunoassay after flicking off the excess water.

0.1 ml of the antiserum diluted with 1% BSA-PBS was dispensed into each well which was allowed to stand at 4° C. overnight. The antiserum solution was flicked out and the well was washed 6 times with 2M NaCl-PBS, followed by washing with tap water.

After flicking out the water, rabbit anti-mouse IgG Fab antibody which had been specifically purified by using an immunoadsorbent and labelled with $^{125}$I, was diluted with 1% BSA—PBS and each 0.1 ml (50,000 dpm/20 ng as specific antibody protein) of the diluted solution was dispensed into each well and allowed to stand at 4° C. overnight. If there is any antibody capable of binding with an antigen on the surface of polyvinyl, then the antibody will be coupled with the antigen. The presence or absence of such an antibody can be detected by the degree of coupling of the rabbit anti-mouse IgG Fab antibody labelled with $^{125}$I. Each isotope solution in the well was removed by using a pipette. After washing throughly with water, the flexible plate was placed in a plastic rigid plate, and the top of the flexible plate was cut off with hot wire, and then the radioactivity in each well was counted.

Figure 1:
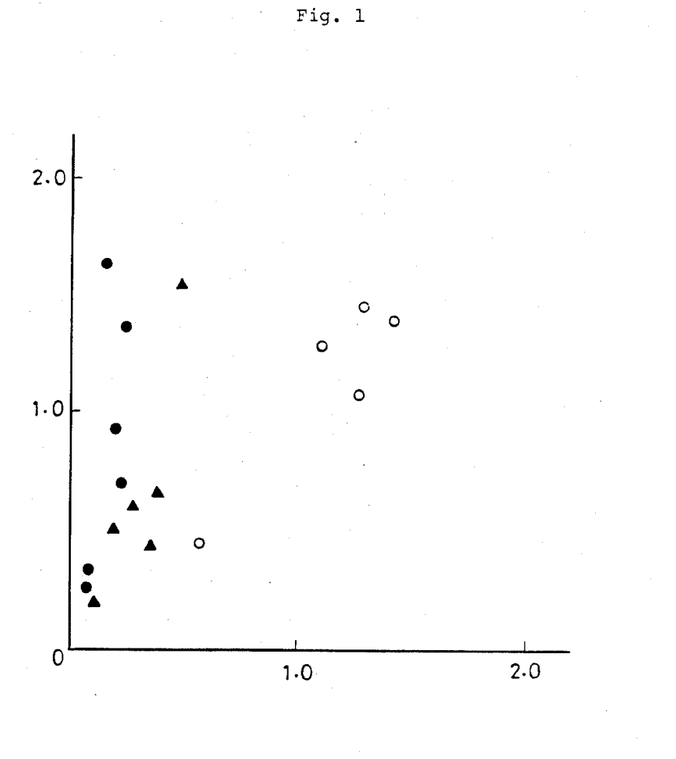

(C) Results:

At each time of collection of the serum, the antibody titre of the pooled serum from the mice of each group was assayed. Samples collected 11 weeks after the primary immunization contained maximum levels of antibody. Therefore, antibodies in the antisera collected 11 weeks after primary immunization were subjected to further detailed analysis.

In this measurement, pooled antiserum from group 1 collected 7 weeks after the primary immunization was used as the standard antiserum. The amount of antibody in the test sample obtained from individual mice at 11 weeks was expressed as the ratio to the amount of antibody contained in the standard antiserum which was defined as 1 unit. The titre of the standard serum was as follows. When assayed by the following liquid phase radioimmunoassay method using CCK-8-P, this serum (with ×600 dilution) was capable of binding 0.0015 pmol of CCK-33.

With regard to the antibodies obtained from the mice of the first group, to which no pentagastrin$_{15}$-D-GL was administered, (shown by the mark "o" in FIG. 1) the amount of antibody reacting the CCK-8-P and the amount of antibody reacting with pentagastrin were almost equal. It was found that antibodies obtained from the mice administered with pentagastrin$_{15}$-D-GL (i.e. the second and third groups of mice shown by the marks "▲" and "o" in FIG. 1, respectively) showed a very low titre of antibody reactive with pentagastrin. In particular, the antibodies obtained from the mice of the third group, to which pentagastrin$_{15}$-D-GL was given after the primary immunization (i.e. 3 days before the secondary and tertiary immunizations) showed an extremely low titre of antibody reactive with pentagastrin.

Each value is conveniently expressed as a ratio of each amount of antibody to that present in the pooled serum collected from mice of the first group 7 weeks after the primary immunization.

From these results, it is apparent that by use of the present invention, an antibody having a specificity for the specific amino acid sequence of CCK-8-P i.e.

has been obtained.

EXAMPLE 7

The cross-reactivities of the antibodies obtained above were determined by liquid phase radioimmunoassay system which allows the coexistence of CCK-8-P and pentagastrin. CCK-8-P was labelled with $^{125}$I using Bolton-Hunter reagent [H. Sankaran et al, J. Biol. Chem., Vol. 254, 9349-9351 (1979)] and hereinafter referred to as $^{125}$I-BH-CCK-8-P. 50 μl of 0.02M phosphate buffer solution (pH=8.0; containing 1% gelatin) containing various amounts of unlabelled CCK-8-P was added to small test tubes to establish a CCK-8-P standard curve. Separately, 50 μl of a buffer solution containing various amounts of pentagastrin was added to a small tube to establish a pentagastrin standard curve.

On each occasion, antiserum (50 μl) diluted with normal mouse serum was added to the test tubes, to which was then added the same phosphate buffer solution (50 μl) containing $^{125}$I-BH-CCK-8-P (about 5000 cpm) and the solution was well mixed using a vortex mixer, followed by incubating at 4° C. for 24 hours. After this, 50 μl of rabbit anti-mouse IgG Fab antibody diluted to 1:2 with the same phosphate buffer was added to the test tubes, mixed and incubated at 4° C. for 24 hours. After this, the test tubes were centrifuged (3000 r.p.m.) for 25 minutes. The supernatant was aspirated, and the radioactivity of the precipitate counted in a counter.

Instead of the standard solutions of CCK-8-P and pentagastrin, the same phosphate buffer was used in order to determine the radioactivity of total $^{125}$I-BH-CCK-8-P (count, $B_0$, expressed as 100), and the bound ratios ($B/B_0\%$) of the antibody with $^{125}$I-BH-CCK-8-P in the presence of CCK-8-P or pentagastrin at different concentrations were calculated.

The molar amounts of various peptides required for 50% inhibition of binding of the antibody with $^{125}$I-BH-CCK-8-P are as follows.

In the first group, CCK-8-P was 1.1 pmol, and pentagastrin was 20.1 pmol. Thus, the cross-reactivity calculated by Abraham's method was 5.5% ($1.1/20.1 \times 100$).

In the second group, in which pentagastrin$_{15}$-D-GL was administered before the primary immunization, the cross-reactivity was 2.7% ($4 \text{ pmol}/150 \text{ pmol} \times 100$).

In the third group, in which pentagastrin$_{15}$-D-GL was administered after the primary immunization, i.e. 3 days before the secondary and tertiary immunization, no cross-reactivity with gastrin was found. That is, 1.7 pmol of CCK-8-P was required for 50% inhibition when the said antibody was used, but no inhibition was found by 10,000 pmol of pentagastrin. This means that pentagastrin is actually incapable of reacting with the antibody produced by the mice of the third group.

From these results, it is apparent that CCK-8-P may be specifically assayed without significant effect of coexisting pentagastrin by using the antibodies originating from the mice of the third group, to which pentagastrin$_{15}$-D-GL had been administered.

EXAMPLE 8

A similar procedure to that described in Example 6 was repeated except for the use of rabbits instead of mice.

By the use of complete or incomplete Freund's adjuvant containing 100 μg of CCK-8-P-KLH and 10 ml of saline containing 10 mg of pentagastrin$_{15}$-D-GL, the results obtained were substantially similar to the results obtained by the use of mice.

EXAMPLE 9

The same procedure of Example 6 was repeated except for the substitution of pentagastrin$_{15}$-D-GL with pentagastrin$_{33}$-D-GL of molecular weight of 115,000. The results obtained are substantially the same as the results obtained by Example 6.

EXAMPLE 10

Preparation of anti-CCK-8-P specific antibody-producing clones:

(A) Procedure:

The spleen cells (each $2 \times 10^8$) of mice of the first (control) and third (treated with pentagastrin-D-GL) groups immunized by the method of Example 6 (A) were respectively used as starting materials. On each occasion, the cells were fused with P3-X63-Ag80-U1 (P3U1) tumour cells ($2 \times 10^7$) in polyethylene glycol 4000. The cell pellets were loosened and diluted with a PEG solution [a mixture of 9 g of PEG 4000 and 20 ml of HANKS] in order to prepare a cell suspension. The cell suspension was allowed to stand at room temperature for 8 minutes, and MEM (15 ml) was slowly added to the cell suspension in 5 minutes, followed by addition of MEM to make up to 50 ml in total. The cells were spun out from the suspension and were further treated in a 10% FCS-RPMI (50 ml) and distributed over a culture cup (1 ml/well) for culturing at 37° C. overnight by using a humidified $CO_2$ incubator containing $CO_2$ (7%) in air having a relative humidity of 85–95%. Every morning of the next two days, HAT medium (1 ml) was sucked out from the well and replaced by fresh HAT medium (1 ml). A similar replacement was effected for the next two weeks at 3 days interval. After this, the cultured broth was taken out and was assayed to determine the antibody secretion by using the solid phase radioimmunoassay method described in Example 6 (B). For cloning, the limiting dilution of the positive culture media was effected by using a 10% FCS-RMPI. The cultured broth containing clones was assayed by the solid phase radioimmunoassay method described in Example 6 (B) to determine the specificity of the antibodies produced by the thus-produced clones.

(B) Results:

By using the spleen cells of the mice of the first group, there were obtained 18 clones capable of producing anti-CCK-8-P antibody. All of the thus-obtained antibodies were reactive with both CCK-8-P and pentagastrin. Thus, it was found that the antibodies thus-obtained were monoclonal antibodies which were specific to the pentagastrin portion of CCK-8-P. On the other hand, by using the spleen cells of the third group, there were obtained 15 clones capable of producing anti-CCK-8-P antibody. Among these 15 clones, 12 clones were capable of producing anti-CCK-8-p antibodies which were not reactive with pentagastrin and other related peptides and specific to CCK-8-P, whilst the antibodies produced by the remaining 3 clones were cross-reactive with pentagastrin. Thus, by using the spleen cells of the mice treated with the pentagastrin-D-GL of the present invention, it is possible to obtain a larger number of the desired anti-CCK-8-P specific antibody-producing clones than in the cases of using the spleen cells treated in conventional manner. The anti-CCK-8-P specific antibodies thus-obtained exhibited no cross-reactivity with pentagastrin.

What is claimed is:

1. A process for producing an antibody having a high specificity to a first antigen and a low cross-reactivity with at least one second antigen by immunizing a mammal or by culturing mammal cells capable of producing antibodies, said first antigen comprising a desired antigenic determinant and said second antigen comprising at least one antigenic determinant which is structurally related to said desired antigenic determinant of said first antigen, which process comprises administering to a mammal a copolymer of D-glutamic acid and D-lysine coupled with said second antigen thereby inducing a substantially effective immunological tolerance to said second antigen, and then immunizing said mammal with said first antigen.

2. The process of claim 1, wherein said antibody is in the form of an antiserum.

3. The process of claim 1, wherein said antibody is obtained from a clone capable of producing said antibody.

4. The process of claim 1, wherein said mammal is selected from the group consisting of mouse, rate and guinea pig.

5. The process of claim 1, wherein said mammal is selected from the group consisting of rabbit, sheep, goat, pig and cattle.

6. The process of claim 1, wherein said copolymer of D-glumatic acid and D-lysine has a molecular weight of from about 27,000 to about 120,000.

7. The process of claim 1, wherein the molar ratio of D-glumatic acid to D-lysine of said copolymer is from about 70:30 to about 30:70.

8. The process of claim 1, wherein said other antigen is selected from the group consisting of steroid, catecholamine, and peptide.

9. The process of claim 8, wherein said steroid is selected from the group consisting of testosterone, 5α-dihydrotestosterone, androsterone, etiocholanolone, progesterone, 17α-hydroxyprogesterone, pregnenolone, dehydro-epiandrosterone, oestradiol, oestrone, oestriol, aldosterone, deoxycorticosterone, cortisol, cortisone, corticosterone, 11-deoxycortisol, cholic acid, deoxycholic acid, lithocholic acid, and conjugated compounds thereof.

10. The process of claim 8, wherein the catecholamine is selected from the group consisting of dopamine, norepinephrine, epinephrine and derivatives thereof.

11. The process of claim 8, wherein the peptide is selected from the group consisting of gastrin, cholecystokinin-pancreozymin (CCK), insulin, proinsulin, C-peptide, glucagon, follicle-stimulating hormone (FSH), lutenizing hormone (LH), human chlorionic gonadotropin (HCG), somatostatin, thyroid stimulating hormone (TSH), subunits thereof and related peptides thereof.

12. The process of claim 8, wherein said pharmaceutical agent is selected from the group consisting of l-propanolol and l- and D-cyclazocine.

13. A process for producing an antibody having a high specificity to a first antigen and a low cross-reactivity with at least one second antigen, said first antigen comprising a desired antigenic determinant and said second antigen comprising at least one antigenic determinant which is structurally related to said desired antigenic determinant of said first antigen, which process comprises administering to a mammal a copolymer of D-glumatic acid and D-lysine coupled with said second antigen thereby inducing a substantially effective immunological tolerance to said second antigen, immunizing said mammal with said first antigen whereby to form a cell capable of producing the desired antibody, isolating the cell from said mammal and culturing the cell whereby to obtain the desired antibody.

14. The process of claim 13, further comprising the steps of forming a hybridoma combining the thus-isolated cell with a myeloma and implanting said myeloma into second mammal having the same genetic constitution as that of said first mammal.

15. A process for immunoassay of a substance serving as antigen, which comprises reacting said substance with an antibody produced by the process of claim 1 or 13, separating said antigen from the resulting immune complex of said antigen and said antibody and determining the activity of said first antigen.

16. The process of claim 15, wherein the immunoassay is effected by radioimmunoassay.

17. A clone produced by the process as claimed in claim 3 or claim 13.

* * * * *